United States Patent [19]

Carlson et al.

[11] Patent Number: 5,030,568
[45] Date of Patent: Jul. 9, 1991

[54] BIOCONVERSION OF NAPHTHALENE MONOMERS

[75] Inventors: Ting L. Carlson, Rochester; Karen E. Hesselroth, St. Paul, both of Minn.

[73] Assignee: Minnesota Mining and Manufacturing Company, St. Paul, Minn.

[21] Appl. No.: 506,181

[22] Filed: Apr. 9, 1990

Related U.S. Application Data

[62] Division of Ser. No. 415,034, Sep. 29, 1989.

[51] Int. Cl.$^5$ .......................... C12P 39/00; C12P 7/44; C12R 1/40
[52] U.S. Cl. ...................................... 435/42; 435/142; 435/252.34; 435/877
[58] Field of Search ...................... 435/142, 42, 252.34, 435/877

[56] References Cited

U.S. PATENT DOCUMENTS 3,340,155  9/1967  Douros, Jr. et al. ................ 195/28
4,540,103  5/1985  Ensley, Jr. ......................... 435/121

OTHER PUBLICATIONS

Amoco Bulletin FA-4a R0686, Amoco Chemicals Co., Chicago, Ill.
Davey et al., *J. Bacteriol.*, 119:923-929 (1974).
DeFrank et al., *J. Bacteriol.*, 129:1356-1364 (1977).
Williams et al., *J. Bacteriol.*, 120:416-423 (1974).
Franklin et al., *Mol. Gen. Genet.*, 177:321-328 (1980).
Worsey et al., *J. Bacteriol.*, 124:7-13 (1975).
Kunz et al., *J. Bacteriol.*, 146:179-191 (1981).
Gibson et al., *Biochem.*, 7:2653-2662 (1968).
Cane et al., *J. Gen. Microbiol.*, 128:2281-2290 (1982).
Yen et al., *Proc. Natl. Acad. Sci. USA.*, 79:874-878 (1982).
Ensley et al., *Science*, 222:167-169 (1983).

*Primary Examiner*—Herbert J. Lilling
*Attorney, Agent, or Firm*—Gary L. Griswold; Walter N. Kirn; Philip M. Goldman

[57] ABSTRACT

The conversion of 2,6-dialky naphthalene to the corresponding 2,9-dicarboxy naphthalene by microbiological means is described. Exemplary means include the use of NAH7 plasmids, encoding aromatic oxygenase enzymes, in a Pseudomonas host. The conversion product is useful as a monomer in the production of high performance synthetic polymers.

6 Claims, No Drawings

BIOCONVERSION OF NAPHTHALENE MONOMERS

This is a division of application Ser. No. 07/415,034 filed Sept. 29, 1989.

TECHNICAL FIELD

The present invention relates to the preparation of naphthalene-containing polymers, and to the conversion of naphthalene compounds in order to form monomers useful for preparing such polymers. This invention also relates to microorganisms capable of carrying out biological conversions of monomers, as well as plasmids useful for transforming such microorganisms and methods of preparing such monomers using such transformed microorganisms.

BACKGROUND ART

Monomers such as 2-carboxy-6-alkyl naphthalene ("CAN") and 2,6-dicarboxynaphthalene ("DCN") have been described as useful for the production of a variety of synthetic polymers. DCN has been described, for instance, as an alternative to terephthalate for the production of polyester films. See, e.g., Amoco Bulletin FA-4a R0686, Amoco Chemicals Co., Chicago, Ill. Films prepared from DCN can exhibit improved properties over those prepared from terephthalate, e.g., in terms of their glass transition temperature, tensile strength, gas permeability, and UV resistance.

Currently however, the use of such naphthalene-derived monomers is somewhat limited, partly in view of the high cost of preparing such monomers. Chemical synthesis of DCN is difficult and expensive, in that it typically requires extreme reaction conditions, and results in mixed oxidation products.

The production of organic compounds by means that include one or more biological conversions, i.e., biotransformations, has been proposed as a desirable alternative to the synthesis of compounds that are difficult and/or expensive to prepare chemically. Production by biological means is not always a feasible alternative however, in that it requires the fortuitous identification of naturally-occurring microorganisms or genetic material coding for enzymes capable of carrying out the desired biological conversions, or the creation of such microorganisms or genetic material, e.g., by mutagenesis or by recombinant DNA techniques.

A number of publications teach the degradation of aromatic compounds such as naphthalene or mono-substituted naphthalenes by biological means, e.g., using microorganisms capable of utilizing the compounds as a carbon source.

For instance, the bacterial oxidation of methyl substituents on aromatic rings is not uncommon. (See, e.g., Davey, et al., *J. Bacteriol.* 119:923-929 (1974), DeFrank, et al., *J. Bacteriol.* 129:1356-1364 (1977), and Williams, et al., *J. Bacteriol.* 120:416-423 (1974)). Usually, the methyl group is first oxidized to a carboxyl group, followed by a ring-opening step. (See, e.g., Williams et al., ibid., as well as Franklin, et al., *Mol. Gen. Genet.* 177:321-328 (1980), and Worsey, et al., *J. Bacteriol.* 124:7-13 (1975)). For substrates having more than one methyl group, typically only one such group is oxidized before the ring-opening step. (See, e.g., Franklin, et al., ibid., as well as Kunz, et al., *J. Bacteriol.* 146:179-191 (1981).

In some situations the ring-opening step may occur without the oxidation of the methyl group. See, e.g., Gibson, et al., *Biochem.* 7:2653-2662 (1968). For instance, Cane, et al., *J. Gen. Microbiol.* 128:2281-2290 (1982) describe a naphthalene dioxygenase that preferentially attacks the unsubstituted ring of 2-methyl naphthalene, in order to open the ring without oxidizing the methyl group.

Various plasmids have been identified as responsible for carrying genes coding for the enzymes involved in biological conversions. Of particular interest is a plasmid originally derived from *Pseudomonas putida* and designated the NAH7 plasmid, which carries, inter alia, two gene clusters that enable organisms bearing and expressing the plasmid to grow on naphthalene (nah+) as a sole carbon and energy source. (See, e.g., Yen, et al., *Proc. Natl. Acad. Sci. U.S.A.* 79:874-878 (1982), and Ensley, et al., *Science* 222:167-169 (1983)). U.S. Pat. No. 4,520,103 describes the use of the dioxygenase enzyme(s) of the "NAH7" plasmid for the microbial synthesis of indigo in indole-free media.

U.S. Pat. No. 3,340,155 describes a *Streptomyces* strain capable of converting a dialkyl naphthalene to a carboxy alkyl naphthalene ("CAN"). The conversion was quite slow however, e.g., a 120 hour incubation (about 5 days) for the conversion of 2,6-dimethyl naphthalene to the corresponding mono-carboxy acid. No recovery of the corresponding dicarboxy was described.

None of these references teach a microorganism or plasmid that is capable of oxidizing a dialkylnaphthalene in order to produce a dicarboxynaphthalene. The ability to prepare DCN by biological means, and/or to prepare CAN by more efficient biological means than previously described in the art, would be highly desirable, in that it would provide a relatively safe, efficient, inexpensive and convenient method of producing such monomers for use in polymer synthesis.

SUMMARY OF THE INVENTION

The present invention provides a process for the microbiological production of 2,6-dicarboxy naphthalene ("DCN") by the use of a microorganism grown in a medium containing 2,6-dialkyl naphthalene ("DAN"), and also provides a more efficient process for the microbiological production of the intermediate, 2-carboxy 6-methyl naphthalene ("CAN"). The process of the present invention involves using a microorganism that has been selected from nature or genetically transformed to incorporate the capacity to synthesize one or more aromatic oxygenase enzymes. Oxygenase enzymes useful in the present invention are those known to catalyze microbial oxidation transformation of naphthalene. The microorganisms are grown under conditions that facilitate the oxygenase enzyme transformation of DAN.

In a presently preferred embodiment, microbiological production of CAN and/or DCN is accomplished using *P. putida* as the host cell microorganism. The *P. putida* is transformed with a DNA vector, e.g., a plasmid, that includes a DNA sequence coding for the expression of naphthalene oxygenase, which is an aromatic oxygenase of *Pseudomonas* origin and is coded for by the plasmid NAH7.

In a further aspect, this invention provides the naphthalene monomers produced microbiologically, as well as polymers prepared from such monomers.

DETAILED DESCRIPTION OF THE INVENTION

The word "bioconversion", and inflected forms thereof, as used herein, refers to the conversion of 2,6-dialkyl naphthalene ("DAN") by microbiological means to either the 2,6-dicarboxy naphthalene ("DCN") or to a mixture of DCN and an intermediate 2-carboxy 6-alkyl naphthalene ("CAN").

The bioconversion according to the method of the present invention can be achieved using DNA sequences of either chromosomal or plasmid origin. Examples of suitable DNA sequences include a gene or genes coding for suitable oxygenase enzyme(s), e.g., those that recognize aromatic substrates. Such DNA sequences can be obtained, e.g., by selection from nature; by mutagenesis; or by recombinant methods practiced on microbial species. Preferred are those microbial species that display the ability to transform a dialkyl naphthalene without degradation, i.e., without opening the aromatic ring thereof. A preferred DNA sequence is the transmissible naphthalene-degrading plasmid, NAH7, discovered originally in the species *P. putida.* The NAH7 plasmid is available from a variety of sources, e.g., from the *P. putida* strain having accession number ATCC 17485, American Type Culture Collection, Rockville, Md.

The preferred plasmids of the invention can be used in a variety of ways to transform microorganisms, e.g., by conjugation techniques known to those skilled in the art. The recipient microorganism need only have the ability to be transformed, i.e., to accept and express the necessary genes of the plasmid in such a manner that the resultant transformed microorganism is able to oxidize an alkyl-substituted naphthalene to the corresponding carboxy-substituted naphthalene.

For instance, the NAH7 plasmid can be transferred by conjugation into a microbial strain having a demonstrated ability to degrade naphthalene. Examples of suitable recipient strains include Pseudomonas strains, and particularly *P. putida* strains that meet the above requirements. A preferred strain for this purpose is the *P. putida* strain identified as "PaW 340" that is described, for example, in Cane, et al., *J. Gen. Microbiol.* 128:2281-2290 (1982). PaW 340 is preferred in that it does not contain any other plasmids, thus making the presence of the NAH7 readily detectable.

Cells transformed with the NAH7 plasmid are then grown in a naphthalene-containing environment in order to maintain the presence of the plasmid in the cells. For present purposes, the cells are streaked onto a solid carbon-free medium contained in the bottom of a Petri dish. The dish is then inverted and placed within its lid, which contains naphthalene crystals, in order to allow the naphthalene vapors to saturate the atmosphere within the closed Petri dish. After suitable incubation, cell growth is generally confluent on the surface of the medium.

Cells are transferred from the surface of the carbon-free medium, e.g., with a bacteriological loop to a rich broth, such as Luria-Burtani ("LB") described below, in order to increase the cell mass. Cells are spun down by centrifugation and resuspended in minimal medium.

As described more fully in the EXAMPLES below, the cells are then preferably induced by adding to the cell-containing minimal medium one or more suitable carbon sources together with one or more suitable inducers. The word "inducer", as used herein, refers to a compound that substantially increases the amount and/or activity of enzyme(s) of interest. See, e.g., Barnsley, E. A., *J. Gen., l. Microbiol.* 88:193-196 (1975), the disclosure of which is incorporated herein by reference. Suitable inducers can be determined in the manner described in the EXAMPLES below. Preferably inducers are used in a medium that also contains one or more carbon sources such as acetate, benzoate, salicylate, and yeast extract together with the inducer itself, e.g., a substituted or unsubstituted aromatic inducer such as 2-amino benzoate.

Naphthalene substrate, preferably 2,6-dimethyl naphthalene, is also introduced into the cell suspension at any suitable time, e.g., simultaneously with or shortly after the addition of carbon source and inducer. Substrate can be introduced in any suitable form, e.g., as crystals or dissolved in a solvent such as methanol or dimethyl formamide. Substrate in the form of crystals is presently preferred, wherein the crystals float on the top of the medium, allowing more substrate to dissolve into solution as the bioconversion proceeds.

The suspensions are then incubated under conditions suitable for the cells to carry on the bioconversion of the DMN. The course of conversion can be monitored, and the final products can be harvested, e.g., purified, as described in the EXAMPLES below. Typical conditions include incubation at 30° C., with shaking, for on the order of up to 7 days.

The invention will be further described by the following non-limiting EXAMPLES. Unless otherwise indicated, all percentages are weight/volume.

EXAMPLE 1

Strain Development

The naphthalene-degradative plasmid, NAH7 (designated "pNAH"), obtained from American Type Culture Collection Accession No. 17485) was transferred to *P. putida* 3CB5 (obtained from the culture collection of Peter Chapman, University of Minnesota) by conjugation. See "Gene Transfer", Roy Curtis III, Chapt. 14, pp. 256-262, in *Manual of Methods for General Bacteriology*, Gerhardt, ed., American Society for Microbiology (1981), the disclosure of which is incorporated herein by reference. The resultant strain, designated "3CB5(pNAH)", was a 3-chlorobenzoate degrading strain containing a naphthalene degradation plasmid, and was used further as described below in an attempt to create strains that could oxidize 2,6-dimethyl naphthalene ("DMN") to 2-carboxy 6-methyl naphthalene ("CMN") and DCN.

Spontaneous mutants that were able to grow on substituted naphthalenes, e.g., 2-methylnaphthalene or 2-chloronaphthalene, were selected. About $10^9$ cells of sub-strain 3CB5-2(pNAH), a mutant strain that grows on 2-methylnaphthalene plate, and of sub-strain 3CB5-3(pNAH), a mutant strain that grows on 2-chloronaphthalene plate, were patched onto carbon-free minimal medium plates with 2,6-dimethyl naphthalene ("DMN") crystals as the substrate. Two to three tiny colonies appeared on each plate after 2 weeks of incubation at 30° C., indicating the ability to utilize the substrates and thus gain a slight advantage over background cells. One colony from 3CB5-2(pNAH) was purified by growing on rich medium and designated *P. putida* 1012, and one colony from 3CB5-3(pNAH) was similarly purified and designated *P. putida* 1013.

Purified *P. putida* 1012 and 1013 were strengthened by grown in a rich medium, i.e., a "Luria-Burtani" agar plate, prepared as follows:

| Bacto-tryptone | 10 g/L |
|---|---|
| Yeast Extract | 5 g/L |
| NaCl | 10 g/L |
| Agar | 15 g/L |
| Adjust pH to 7.5. Sterilize. | |

(See Maniatis, et al., "Molecular Cloning: A Laboratory Manual", p. 440, Cold Spring Harbor (1982), the disclosure of which is incorporated herein by reference.) The cells were then maintained on minimal medium agar plates with naphthalene vapors as the growth substrate. Although both strains were capable of performing the conversion of DMN to CMN and DCN, strain 1013 appeared to be a somewhat better producer of DCN.

In order to determine whether the gene for the oxidase responsible for the above conversion was still plasmid-borne, the plasmid from strain 1013 (designated p1013) was conjugally transferred into a plasmid-free *P. putida* strain, PaW340 (obtained from the culture collection of P. Chapman, University of Minnesota). When p1013 was transferred from strain 1013 to PaW340, the resultant plasmid-carrying PaW340 strain developed the ability to convert DMN to DCN, suggesting that the oxidase performing this conversion remained plasmid-borne.

Plasmids p1013 and pNAH were digested by restriction enzymes EcoRI and HindIII. Electrophoresis in 1% agarose showed no apparent difference in the fragmentation patterns of the 2 plasmids, consistent with p1013 being a derivative form of pNAH. It was further found that the oxidizing capability was co-transferred into the new host strains and it was encoded in both pNAH and p1013. Similar amounts of CMN and DCN were obtained with the transconjugate strains and 1013.

Whole cell oxidation analysis was conducted polarographically using a Clark-type oxygen electrode at 30° C. (See generally, Kleka, et al., *Appl. Environ. Microbiol.* 41:1159–1165 (1981)). Cells of *P. putida* were grown in liquid basal medium ("BM") prepared as follows:

| Basal Medium ("BM") | | | | |
|---|---|---|---|---|
| Prepare buffer as follows: | | | | |
| $K_2HPO_4.3H_2O$ | 4.25 g | or | $K_2HPO_4$ | 3.2450 g |
| $NaH_2PO_4.H_2O$ | 1.00 g | or | $NaH_2PO_4$ | 0.8875 g |
| $NH_4Cl$ | 2.00 g | | | |
| $H_2O$ | 900 ml | | | |
| Adjust to pH = 7.2. Sterilize. | | | | |
| Prepare trace metals (10X stock solution) as follows: | | | | |
| Nitrilotriacetic acid (NTA) | 1.00 g/L | | | |
| $MgSO_4.7H_2O$ | 2.00 g/L | | | |
| $FeSO_4.7H_2O$ | 0.12 g/L | | | |
| (or $FeSO_4$, 0.0656 g/L) | | | | |
| $MnSO_4.7H_2O$ | 0.03 g/L | | | |
| $ZnSO_4.7H_2O$ | 0.03 g/L | | | |
| $CoSO_4.H_2O$ | 0.01 g/L | | | |
| (or $CoCl_2.6H_2O$, 0.0137 g/L) | | | | |
| Sterilize. | | | | |
| Add 100 ml trace metal stock solution to 900 ml of buffer. | | | | |

Cells were incubated overnight in BM in a 30° C. shaker with the addition of sodium acetate (0.1%, final concentration) as the carbon source and 2-aminobenzoate (0.005%, final concentration) as inducer. The cells were washed with 0.05M Tris-HCl buffer, pH 7.5, and resuspended in 1% of the original culture volume of Tris buffer. Each reaction contained: 1.4 ml of 0.05M Tris-HCl, pH 7.5; 0.01 ml of 0.1M naphthalene substrate dissolved in N,N-dimethylformamide; 0.1 ml of 0.03M NADH solution, and 0.02 ml of the cell suspension. The consumption of NADH was followed by High Pressure Liquid Chromatography ("HPLC").

As can be seen in TABLE 1, whole cell oxidation analysis revealed that strains 3CB5(pNAH) and 1013(p1013) exhibit different patterns of oxygen consumption using different substrates. Oxygen consumption is an indication of oxidase enzyme activity, so although by electrophoresis the DNA sequences resulting in these enzymes appears to be the same, differences in oxygen consumption, and presumably enzyme activity, are apparent. The enzyme activity differences, in light of similar plasmid restriction maps, suggest that there may be mutation(s) leading from 3CB5(pNAH) to 1013(p1013). Such mutation(s) may be, for instance, single base pair changes or other mutations of a regulatory nature, rather than a deletion or addition of DNA sequences that would be detectable by restriction mapping.

Another noticeable difference between the strains was the color development during 2-chloronaphthalene oxidation. Strain 3CB5(pNAH) converted this substrate to a yellow, ring-fission product which was not further degraded. With the 1013 (p1013) strain, the yellow color (indicating a meta-ring fission degradative pathway) appeared but after another hour or so incubation faded away, indicating further conversion to other, uncolored, products.

The 1,2- and the 1,6-isomers of dimethylnaphthalene were oxidized by strain 1013(p1013), as seen in TABLE 2, however both were accompanied by the formation of slightly yellow color, indicating that both were oxidized through the meta-ring fission naphthalene-degradative pathway. No such color formation was apparent using the 2,6- or 2,7-DMN isomers however, even after overnight incubation indicating no further ring fission steps.

Conversion of Dialkyl Naphthalene

Conversions by strain 1013(p1013) were performed in liquid basal medium ("BM"), prepared as described above, using 0.1% by weight sodium acetate as the sole carbon source, in a shaker at 30° C.

A mixture of dimethylnaphthalene substrates (Aldrich Chemical Co., Cat. No. 12,653-5) were added to the liquid cultures as crystals (final concentration by weight 0.1%) or as 1% (by weight) methanol solutions (0.005% or 0.0025% by weight final concentration). HPLC performed as described below on cell culture supernatent indicated that approximately four times more CMN was produced from 0.1% crystalline DMN than from 0.005% DMN in methanol. No difference in CMN production was found between the substrate concentrations of 0.005% and 0.0025% in methanol. The concentration of CMN did not increase after 2–3 days of incubation in any of the three cases. It was found that approximately twice as much DCN was produced with crystalline DMN as compared to the 0.0025% DMN methanol solution.

To determine whether or not the products were inhibiting the oxidation reaction, CMN (0.004%) and DCN (0.001%) were added to cell suspensions along with the initial addition of DMN. No inhibition was observed.

Analytical Methods

Cultures were monitored daily by HPLC using a C18 reversed phase column (5 μm pore size, 100 mm×4.6 mm, Brownlee Labs, Inc., Santa Clara, CA) treated with an ion-pairing reagent, dodecyltriethyl ammonium phosphate (Q-12, Regis Chemical Co., Morton Grove, IL). The Q-12 system required only one isocratic phase (51.8% methanol, 48.2% 0.1 M ammonium acetate, pH 6.8, 2.5 mM Q-12) to see both the very polar diacid and the less polar methylated monoacid in the same chromatogram. The peaks that correspond to DCN and MCN eluted at 2.42 minutes and 10.73 minutes, respectively. Following removal of these compounds by acid precipitation a chromatogram of the supernatant showed only the peaks of unrelated metabolites.

PRODUCT RECOVERY AND CONFIRMATION

In order to confirm HPLC findings, following incubation the cultures were centrifuged at 9000 rpm, after which the supernatant was filtered through 0.3 μm filters to remove any remaining cells. The filtrate was acidified to pH 1-2 using sulfuric or hydrochloric acid, refrigerated overnight to maximize precipitation, then centrifuged again and quickly rinsed with 70% ethanol.

The metabolites were derivatized with either $BF_3$ methanol (Pierce Chemical Co., Rockford, Ill.) or N,O bis(trimethylsilyl)trifluoroacetamide (Pierce Chemical Co., Rockford, Ill.) before analysis by GC/MS. The position of the substituents on the naphthalene ring was determined by nuclear magnetic resonance (NMR) techniques.

The precipitate yielded the naphthalene mono- and diacids, plus some fatty acids, as confirmed by conventional gas chromatography/mass spectrometry ("GC/MS") analysis. The positions of the substituents were the same as in the original substrates, as determined by NMR.

EXAMPLE 2

Selection from Nature

Using a solid minimal medium prepared with "TTC" selection medium prepared as described below and using substrate vapors as a sole carbon and energy source, a sewage component known as "mixed liquor" (Metropolitan Waste Control Commission, St. Paul, Minn.) was screened as described in the PROTOCOL below for cells able to grow using this substrate. Triphenyl tetrazolium chloride ("TTC"), a colorless dye which turns red upon reduction to the insoluble compound formazan was incorporated into the medium (0.0025%) and used to identify the sewage organisms for their ability to oxidize the naphthalene substrate. TTC selection medium was prepared as follows:

| | |
|---|---|
| 0.7% $K_2HPO_4$ | 0.2% proteose peptone #3 |
| 0.3% $KH_2PO_4$ | 0.05% sodium acetate |
| 0.02% $MgSO_4.7H_2O$ | 1.5% agar |
| Adjust pH to 7.2. Sterilize. Add 2.5 ml 1% (w/v) TTC stock solution while agar still liquified. | |

A microbe's ability to oxidize the substrate generates NADH and free electrons, which electrons in turn cause the TTC to turn those colonies red. See, e.g., Lederberg, J., *J. Bacteriol.* 56:695 (1948), the disclosure of which is incorporated herein by reference. The red colonies were purified for further testing. These isolates were then grown in the presence of naphthalene on minimal medium containing no TTC. Since the presence of brown or yellow colonies indicates the presence of organisms capable of degrading the molecules by cleaving the aromatic rings, these isolates were then rejected. The remaining isolates were grown in liquid medium with DMN and screened by HPLC for the ability to produce MCN and DCN. The conversion, product recovery and analytical steps were as described above in EXAMPLE 1.

Many of the resulting strains could oxidize one of the methyl groups to produce MCN, and when these strains were cocultured with 1013(p1013) their presence often enhanced the production of both MCN and DCN (described in more detail in EXAMPLE 6). Two strains, designated 1032 and 1028, respectively, produced MCN and DCN when cultured alone (i.e., without 1013(p1013)), and production by each of these was enhanced when this strain was cocultured with 1013(p1013).

PROTOCOL

A gallon (approximately 3.8 liters) of "mixed liquor" fraction of sewage was obtained. A 300-500 ml sample of this sewage was strained through cheesecloth which was folded so that the liquid flowed through several layers. The filtrate was then filtered through Whatman #4 filter paper. Sixteen 20 ml samples of this filtrate were then filtered using 0.2 μm filter discs, which were then placed on the solid TTC-containing agar plates described below. In the lids of the petri plates of 8 of these plates was placed 2,6-dimethylnaphthalene crystals, and in the other 8 lids, 2-methylnaphthalene crystals. The plates containing the medium with the filter discs were then inverted over the crystal-containing lids. The vapors from the crystals saturated the atmosphere inside the plates, exposing the microorganisms to the compounds. The individual 20 ml samples each contained approximately $10^{10}$ organisms. Growth on every plate was confluent. Of the 8 plates exposed to 2,6-DMN a total of 21 colonies were red. All of these were picked and purified. Each of the 8 plates exposed to 2-methylnaphthalene had about 200 red colonies. About 250 of these were picked and purified. When grown on medium containing no TTC it was evident by the yellow or brown colors produced that many of these microorganisms could cleave the aromatic rings and were therefore considered unsuitable for present purposes and discarded. None of the 2,6-DMN exposed isolates exhibited evidence of the colored ring-fission products. Seven of the remaining isolates from the 2-methylnaphthalene exposed plates and all of the isolates from the 2,6-DMN exposed plates were then grown in broth cultures (as described in EXAMPLE 1) and analyzed by HPLC for the DCN and CMN peaks. Approximately 15 strains isolated from the 2,6-DMN plates and approximately 9 strains isolated from the 2-MN plates showed evidence of CMN production. Strain 1028 and strain 1032, isolated from 2,6-DMN and 2-MN plates respectively, showed any evidence of DCN production. The evidence was subsequently confirmed by GC/MS analysis.

Other strains showing CMN production, but no apparent DCN production, were used in coculture as described below in EXAMPLE 6. The above results indicate that DCN-producing strains can effectively and reproducibly be isolated from the sewage samples used.

EXAMPLE 3

Effect of Inducer

The conversion by 1013(p1013) as described in EXAMPLE 1 was carried out with and without 0.005% 2-aminobenzoate added to the medium. More enzyme was present in the cells exposed to the inducer, and in turn, the use of inducer resulted in detectable DCN production, whereas no DCN production was detected without inducer. The presence of inducer also resulted in a 60% greater production of CMN.

EXAMPLE 4

Effect of Cell Density

Since the use of acetate in the minimal medium did not appear to result in a high cell density, the cells were pregrown overnight in the richer Luria-Bertani broth (LB), centrifuged, then resuspended in the same volume of basal medium. Conversion then proceeded as in EXAMPLE 1. Maximum yields of MCN and DCN could be achieved in 1-2 days incubation in the basal medium, thereby indicating that increasing the cell density increased the amount of enzyme available for the conversion. Pre-growing the cells in LB broth and adding 2-aminobenzoate to the cell suspensions increased the MCN and DCN production by 200% over BM with acetate but without inducer.

EXAMPLE 5

Effect of Nutritionally Stressed Cells

The nitrogen concentration in the conversion medium was limited in order to attempt to stress the cells into looking for alternative energy sources, perhaps encouraging them to consider using the DMN substrate. Low nitrogen medium, containing 8% of the nitrogen of BM, was prepared as follows and used to stress the cells.

| Low Nitrogen Medium | |
|---|---|
| $K_2HPO_4$ | 3.2450 g |
| $NaH_2PO_4$ | 0.8875 g |
| $(NH_4)_2SO_4$ | 0.2000 g |
| $H_2O$ | 900 ml |
| Adjust to pH = 7.2. Sterilize. Add 100 ml sterile trace metals stock solution to 900 ml. | |

In the low-nitrogen medium the accumulation of CMN was increased by approximately 150%. The accumulation of DCN, however, was decreased by approximately 50%.

EXAMPLE 6

Effect of Co-culturing Strains

Strain 1013(p1013) was cocultured with a variety of other microbial strains. Each strain of a coculture was first grown overnight in LB broth and centrifuged. The strains were resuspended together in BM with acetate, inducer, and DMN as described in EXAMPLE 1.

Sewage isolate strains, isolated as described in EXAMPLE 2, but not demonstrating DCN production (designated B41a, B41b, 1015, 1018, 1020, 1029, 1030, 2, 5, 18bl, 18b2, 18b3), as well as strains 1032 and 1028, were found to enhance the production of MCN when cocultured with strain 1013(p1013). Strains B41b, 1029 and 18bl when cocultured with 1013(p1013) produced more DCN in 3 days than 1013(p1013) alone could produce in 6 days. The combination of strains 1020+1013(p1013) produced the highest production of DCN (approximately twice that of 1013(p1013) alone) and coculture of 1013(p1013)+B41b produced the most CMN, again about twice that of 1013(p1013) alone. Coculture of 3 isolates did not significantly increase production over using 2 isolates. The second strain may help 1013(p1013) cope with the toxicity of the substrate or of other metabolites, as evidenced by the fact that healthy cocultures were still generally apparent after 1 day of conversion. In contrast, decreased cell density and increased cell debris in 1 day conversions were observed using 1013(p1013) alone. Since incubation time and the volume of medium used was the same for cocultures as for conversions using 1013(p1013) alone, production costs could be decreased using cocultures.

Strains B41a and B41b are aerobic, nonfermenting, gram-negative rods exhibiting metabolic capabilities resembling Pseudomonas species. Strain 18bl is an aerobic gram-positive spore-forming rod which is characteristic of a Bacillus species.

EXAMPLE 7

Effect of Substrate

A commercial mixture of DMN isomers from Aldrich Chemical Co., Cat. No. 11,241-0, was used as a source of DMN for the production of DCN by strain 1013. The ability to use such a mixture would provide significant cost savings compared to the use of purified substrates. As analyzed by gas chromatography, the mixture consisted of 85.7% DMNs, 6.8% methyl quinolines, 0.9% monomethylnaphthalenes and 4.3% biphenyls; 10.8% of the DMNs was the 2,6-isomer. To aid in interpretation of the mixed isomer experiments, conversions were examined using pure DMN isomers (Aldrich Chemical Co.). The isomers having both methyl groups on the same ring, as well as the 1,6-isomer, were degraded to salicylates via meta-cleavage as judged by the yellow color formation. Naphthalene and monomethylnaphthalenes were degraded to catechol which was then degraded further as judged by the brown color formation. The 1,5- and 1,8-isomers showed no evidence of degradation by these strains as shown by the oxygen consumption assay. 4,4-Dimethylbiphenyl exhibited oxidation of one of the methyl substituents. The product was analyzed and confirmed by GC/MS technique. No quinoline substrates were examined. CMN was only produced by the 2,6- and the 2,7-isomers. DCN was produced only when 2,6-DMN was used as the starting material.

Almost twice as much CMN was produced from a 0.02% DMN mixture than from 0.1% DMN mixture, possibly due to toxicity of the substrate. The accumulation of CMN reached a plateau after 5 days of incubation. A second addition of 0.02% DMN mixture after one day also doubled the final concentration of MCN in the supernatant. It was found that more CMN was formed from the low-nitrogen medium than from the BM medium. However, no DCN was found in either case when DMN mixture was used as the starting material.

TABLE 1

Oxidation of Naphthalene Substrates by
P. putida 3CB5(pNAH7) and 1013(p1013)

| | Oxygen Consumption** | | | |
|---|---|---|---|---|
| | 3CB5(pNAH) | | 1013(p1013) | |
| Substrate | basal | induced | basal | induced |
| nap* | 53 | 100% | 75 | 112 |
| 2-methyl-nap | — | 84.6 | — | 473 |
| 2-chloro-nap | — | 118 | — | 473 |
| 2,6-DMN | — | 87.5 | — | 142 |
| 2,7-DMN | — | 59 | — | 142 |

*nap: naphthalene.
**100% equals to 17 nmols $O_2$/min/20 μl of cell suspension ($10^{10}$ cells/ml). The basal level of oxygen consumption without the addition of substrates is 5 nmols $O_2$/min/20 μl of cell suspension.

TABLE 2

Extent of NADH Consumption by
Induced 1013(p1013) Cell Suspension
Incubated with Various Naphthalene Substrates

| Substrate | Initial NADH remaining after overnight incubation (%) |
|---|---|
| — | 100 |
| nap* | 2.3 |
| 2-methyl-nap | 0.5 |
| 2-chloro-nap | 0.8 |
| 2,6-DMN | 0.95 |
| 2,7-DMN | 4 |
| 1,2-DMN | 0.65 |
| 1,3-DMN | 85 |
| 1,4-DMN | 48 |

TABLE 2-continued

Extent of NADH Consumption by
Induced 1013(p1013) Cell Suspension
Incubated with Various Naphthalene Substrates

| Substrate | Initial NADH remaining after overnight incubation (%) |
|---|---|
| 1,5-DMN | 45 |
| 1,6-DMN | 1 |
| 1,8-DMN | 77 |

*nap: naphthalene.
100% = 2 mM NADH.

What is claimed is:

1. A process for the microbial production of 2,6-dicarboxynaphthalene, said process comprising the steps of;
   (a) obtaining microorganisms of the species Pseudomonas with the ability to synthesize the enzyme naphthalene oxygenase;
   (b) growing said microorganisms in the presence of 2,6-dialkylnaphthalene under conditions facilitative of said enzymatic conversion, and
   (c) isolating 2,6-dicarboxynaphthalene.

2. The process of claim 1 wherein said microorganism is P. putida.

3. The process of claim 1 wherein said naphthalene oxygenase is of Pseudomonas origin.

4. The process of claim 3 wherein said naphthalene oxygenase is encoded for by the NAH7 plasmid.

5. The process of claim 1 wherein said 2,6-dialkylnaphthalene is 2,6-dimethylnaphthalene.

6. A process according to claim 1 wherein said microorganisms are co-cultured with one or more additional microbial strains capable of substantially increasing the total conversion of said 2,6-dialkylnaphthalene.

* * * * *